US007520078B2

(12) United States Patent
Ali et al.

(10) Patent No.: US 7,520,078 B2
(45) **Date of Patent: *Apr. 21, 2009**

(54) ADHESIVE WRISTBAND WITHOUT REMOVABLE COVER SHIELD

(75) Inventors: Sherif M. Ali, Los Angeles, CA (US); Dean D. Peterson, Sylmar, CA (US)

(73) Assignee: Precision Dynamics Corporation, San Fernando, CA (US)

(*) Notice: Subject to any disclaimer, the term of this patent is extended or adjusted under 35 U.S.C. 154(b) by 366 days.

This patent is subject to a terminal disclaimer.

(21) Appl. No.: 11/308,652

(22) Filed: Apr. 18, 2006

(65) Prior Publication Data

US 2007/0157498 A1 Jul. 12, 2007

Related U.S. Application Data

(63) Continuation-in-part of application No. 10/859,030, filed on Jun. 1, 2004, now Pat. No. 7,320,194.

(51) Int. Cl.
*A61B 5/117* (2006.01)

(52) U.S. Cl. .......................................... 40/633; 40/665

(58) Field of Classification Search .................. 40/665, 40/633
See application file for complete search history.

(56) References Cited

U.S. PATENT DOCUMENTS

| | | | |
|---|---|---|---|
| 3,825,463 | A | 7/1974 | Amann |
| 5,364,133 | A | 11/1994 | Hofer et al. |
| 5,457,906 | A | 10/1995 | Mosher, Jr. |
| 5,799,426 | A | 9/1998 | Peterson |
| 2005/0262746 | A1 | 12/2005 | Ali et al. |

*Primary Examiner*—Cassandra Davis
(74) *Attorney, Agent, or Firm*—Kelly Lowry & Kelly LLP.

(57) ABSTRACT

A plurality of identification bracelets removably attached to one another, each bracelet having a first end which includes a cover tab and a second end defining a closure tab having an adhesive portion. The cover tab of a second bracelet removably overlies the adhesive portion of a closure tab of an adjacent first identification bracelet. Upon separating the first and second bracelets, the adhesive portion of the first bracelet is exposed and the cover tab remains with the second bracelet as it is removed. The adhesive portion of the closure tab of the first bracelet is adhered to a surface of the first bracelet as it is moved from an open position to a closed position encircling an object to be identified.

21 Claims, 3 Drawing Sheets

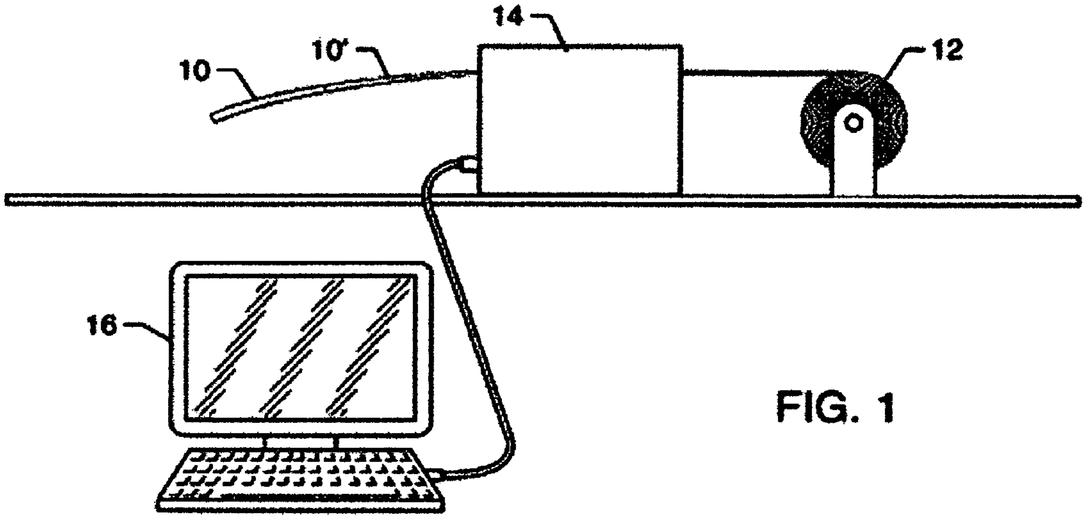
FIG. 1
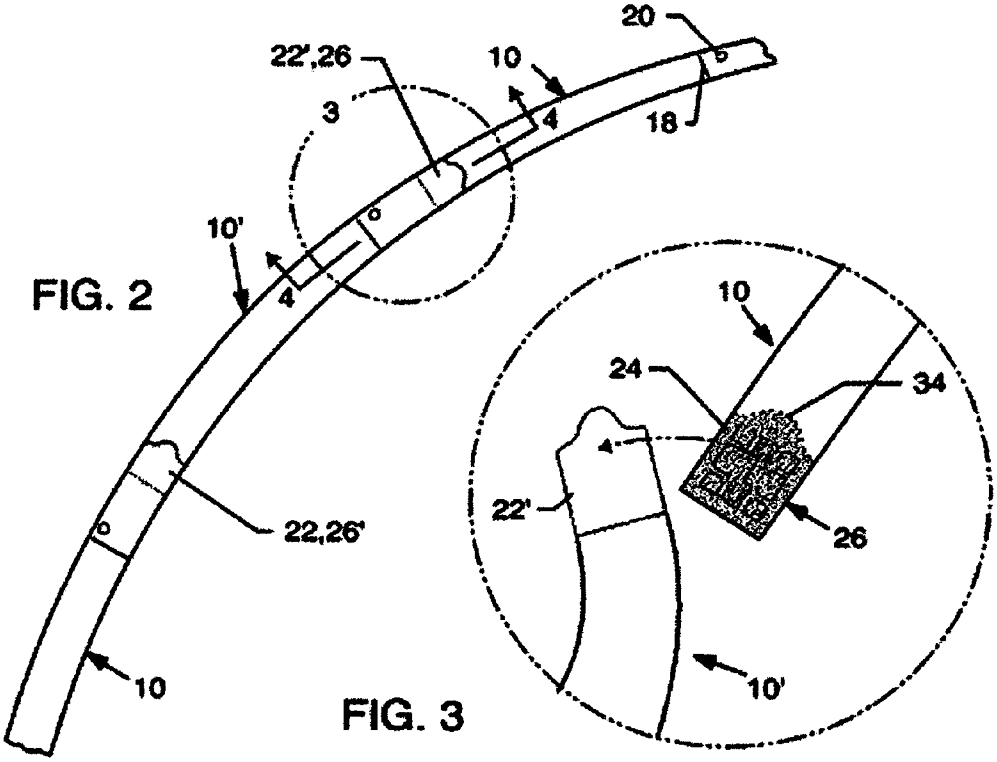
FIG. 2
FIG. 3

ADHESIVE WRISTBAND WITHOUT REMOVABLE COVER SHIELD

BACKGROUND OF THE INVENTION

The present invention generally relates to identification bracelets for identifying persons and/or objects. More particularly, the present invention relates to identification bracelets which are designed such so as to not require a removable cover shield.

The use of identification bracelets is extensive, both in traditional areas such as hospital patient admissions and other applications such as crowd control and patron identification. In addition to being suitably attachable to the person or object to be identified, one of the main requirements of such bracelets is that they must carry appropriate and/or desired information relevant to the person or object to whom the bracelet is attached. Many varieties of bracelets presently meet these two broad criteria.

Various closures are utilized to operatively affix such bracelets to the person or object to be identified. In broad terms, these closures may be described as either mechanical or adhesive. Mechanical closures can increase the cost of the bracelet and typically cannot be fed through a printer, and therefore must be assembled with a bracelet subsequent to the imprinting of information on a bracelet. The downstream assembly process can be cumbersome and inventories of the various components of the mechanical closure must typically be maintained adjacent to the output side of the printer, adding to the administrative burden and time and expense necessary to utilize such systems.

Adhesive closure bracelets can eliminate many of these problems. For example, certain adhesive closure bracelets can be fed through printers. However, the structure of the closures themselves can effect the ability of the printer to accurately print information, especially adjacent to the closure itself. In other words, the additional layers or laminates of materials that are typically utilized to fabricate the closure portion of adhesive closure bracelets, such as removable cover strips that are eventually removed to expose the adhesive prior to attaching the bracelet to a person, can effect the quality and even the feasibility of imprinting information near the closure.

Adhesive closure identification bracelets typically utilize a disposable, throw-away tab or shield which covers the adhesive until just prior to use, at which time the shield is removed from the adhesive and discarded, such as that illustrated and described in U.S. Pat. No. 5,364,133. This presents several disadvantages. The cover tab or shield, sometimes referred to as a removable release liner, becomes waste which must be disposed of in some way. If the shields are not properly disposed of, the separation of the shields from the bands at the point of application can pollute the environment, especially in outdoor applications. Moreover, appropriate disposal (especially in view of the large volumes of bracelets which are frequently used) necessarily requires an increase in the labor associated with the use of the bracelet.

Accordingly, efforts have been made to eliminate the removable cover shield while still presenting an adhesive closure bracelet which is capable of being printed. U.S. Pat. No. 5,457,906 discloses an adhesive closure for an identification band having a shield which is adapted to partially releasably overlie an adhesive portion of the band while remaining engaged with the identification band so as not to be released and become waste. While serving generally adequately, care must be taken not to completely remove the shield when closing the band.

U.S. Pat. No. 5,799,426 discloses a uniform thickness adhesive closure identification bracelet which also avoids the use of removable cover shields. A movable cover portion is formed as part of one of the laminates and is adapted to be moved from a covering relationship to a non-covering relationship with respect to an adhesive disposed between two or more of the laminates. However, care must be taken not to completely delaminate the bracelet.

Thus, there is a continuing need for an adhesive identification bracelet which is capable of being printed in a traditional manner while avoiding the use of removable cover shields. The present invention fulfills these needs and provides other related advantages.

SUMMARY OF THE INVENTION

The present invention resides in an adhesive wristband which is capable of being printed using a traditional printer and which does not utilize a removable and discardable cover shield. The bracelets typically comprise a plurality of bracelets detachably connected end-to-end to form an elongated strip.

A first bracelet comprises first and second diametrically opposed outer sheets, the first sheet having a portion extending beyond a first end of the second sheet, and defining a cover tab. The second sheet extends beyond an end of the first sheet, generally opposite the cover tab, and defines a closure tab having an adhesive portion. The first and second outer sheets are non-removably bonded together substantially between the cover tab and closure tab.

A second bracelet comprises first and second diametrically opposed outer sheets. The first sheet has a portion extending beyond a first end of the second sheet, and defines a cover tab removably overlying the adhesive portion of the closure tab in the first bracelet. The second sheet of the second bracelet extends beyond an end of the first sheet generally opposite the cover tab, and defines a closure tab having an adhesive portion. The first and second outer sheets of the second bracelet are non-removably bonded together substantially between the cover tab and closure tab of the second bracelet.

Upon separating the first bracelet from the second bracelet, the adhesive portion of the closure tab of the first bracelet is exposed and the cover tab of the second bracelet remains with the second bracelet. The exposed adhesive portion of the closure tab of the first bracelet is adhered onto a portion of the first bracelet as it is moved from an open position to a closed position encircling an object to be identified.

A score line formed in the first outer sheet defines the cover tab of the bracelet. An offset score line formed in the second outer sheet defines the end of the bracelet. The score lines may comprise a plurality of perforations.

The first and second outer sheets are each comprised of one or more layers of material. Preferably, at least one of the layers of the first or second outer sheet is comprised of a material adapted to be printed thereon.

Typically, the cover tab and adhesive portion of the closure tab or each bracelet are substantially equal in area. Preferably, a release liner, such as a silicone material, is disposed between the cover tab of the second bracelet and the adhesive portion of the closure tab of the first bracelet. The release liner is adapted to removably adhere the cover tab to the adhesive portion of the closure tab. The release liner may be attached to the cover tab so as to remain with the cover tab as it is removed from the closure tab to expose the adhesive portion.

In a particularly preferred embodiment, an adhesive layer non-removably bonds the first and second outer sheets. The adhesive layer may extend beyond the first sheet towards the end of the second sheet to comprise the adhesive portion of the closure tab.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a diagrammatic view of a spool of identification bracelets embodying the present invention being fed through a computer-controlled printer in accordance with the present invention for identification purposes;

FIG. 2 is a top plan view of a strip of bracelets constructed in accordance with the teachings of the present invention;

FIG. 3 is an enlarged and fragmented view of area "3", illustrating ends of adjoining bracelets being separated from one another;

DETAILED DESCRIPTION OF THE PREFERRED EMBODIMENTS

Figure 4:
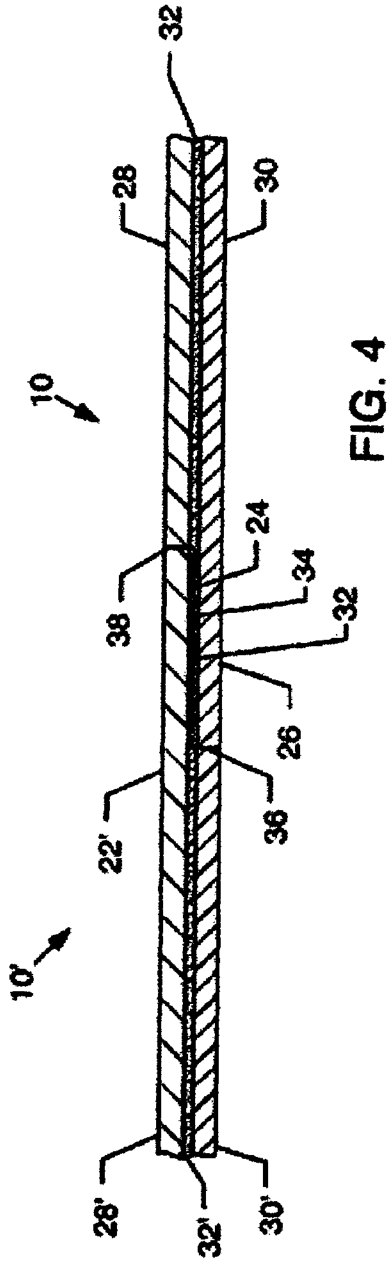
FIG. 4 is an enlarged cross-sectional view taken generally along line 4-4 of FIG. 2, illustrating an overlapping relationship of ends of adjoining bracelets in accordance with the present invention.

As shown in the accompanying drawings for purposes of illustration, the present invention resides in identification bracelets which, as will be explained more fully herein, are detachably connected to one another in elongated strips or sheets and which are designed such that they do not have removable cover shields and the attendant disadvantages thereof.

With reference to FIGS. 1 and 2, a plurality of bracelets 10 are detachably connected end-to-end to form an elongated strip, which can be formed in a spool 12 for feeding through a printer 14 controlled by a computer 16 or the like, as illustrated in FIG. 1. The computer and printer 16 and 14 are preferably capable of imprinting desired identifying information onto each bracelet 10 as the bracelet passes through the printer 14. By way of example, but not by way of limitation, the printer 14 can imprint the Social Security Number, barcoded information, or other information corresponding to the person who will be wearing the bracelet 10 or the event for which the bracelet is used. Such systems can be advantageously utilized in hospital settings, at concerts, at amusement parks, etc. As will be more fully described herein, the bracelets 10 are substantially uniform in thickness so as to be fed through the printer 14 without complication. Each bracelet 10 may include a reflective strip 18 or through-light sensor hole 20. Those skilled in the art will understand that sensors in the printer 14 can utilize the reflective strip 18 or aperture 20 to precisely control the feed of the strip of bracelets 10 through the printer 14 and thereby ensure that the identifying information is imprinted at the desired location along the length of the bracelet 10.

A particularly unique benefit of the present invention is that the bracelets 10 are attached to one another in such a fashion that the need for a removable and disposable cover shield or tab is eliminated. With particular reference to FIGS. 2 and 3, a first bracelet 10 has an end defining a closure tab 26 which has the grippable cover tab 22' of the adjacent bracelet 10' overlying the adhesive portion 24 of its closure tab 26. When the identification bracelets 10 and 10' are separated from one another, such as by gripping cover tab 22' and separating the cover tab 22' and its end of the bracelet 10' from the adjoining end of the bracelet 10 along offset score lines, the cover tab 22' remains with the identification bracelet 10', exposing the adhesive portion 24 of the closure tab 26 of the adjoining identification bracelet 10, as illustrated in FIG. 3. It will be appreciated by those skilled in the art that this arrangement enables and elongated strip of bracelets to be detachably connected to one another and eliminate the need for removable and disposable cover shields, as the cover tab of the adjoining bracelet remains with that bracelet instead of being removed and discarded.

Figure 5:
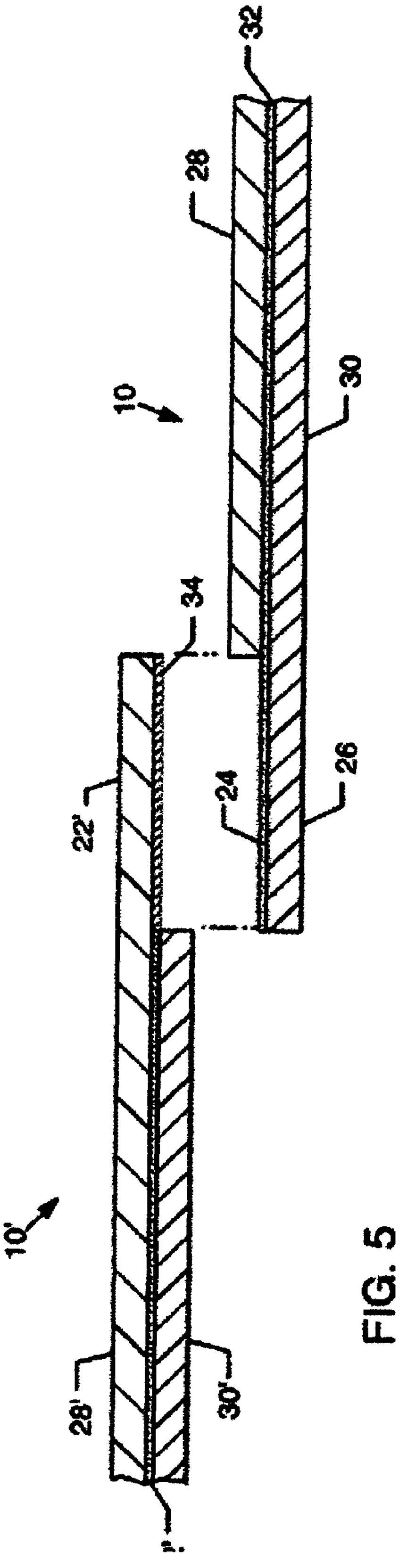
FIG. 5 is a cross-sectional view similar to FIG. 4, illustrating the adjoining bracelets being detached from one another.

With reference to FIGS. 4 and 5, each bracelet 10 is preferably manufactured from a plurality of suitable strong, lightweight, flexible sheets 28 and 30 which are bonded to one another. Of course, it will be appreciated by those skilled in the art that each sheet may be comprised of multiple layers of material which are laminated together or otherwise bonded to one another. For illustration purposes, only the first and second diametrically opposed outer sheets 28 and 30 comprised of a single layer of material are illustrated. The sheets 28 and 30 are relatively permanently bonded to each other by adhesive means, such as an adhesive layer 32. The adhesive portion 24 may be an extension of adhesive layer 32. Those skilled in the art will understand, however, that a wide variety of bonding mechanisms may be used such as sonic welding, heat bonding, etc. such that the sheets 28 and 30 are relatively permanently and non-removably bonded to each other over a majority of the length of the bracelet 10 between the cover tab 22 and closure tab 26. If sheets 28 and 30 are bonded by other means, such as sonic welding or heat, an adhesive patch may be disposed at the end of a bracelet such that the cover tab 22' of an adjoining bracelet 10' would overlie the adhesive patch 24 until the adjoining bracelet 10' was separated, causing the adhesive portion 24 of bracelet 10 to be exposed.

The cover tab 22' of bracelet 10' removably overlies the adhesive portion 24 of the closure tab 26 of bracelet 10. Such removable connection is accomplished with a release liner 34, which adequately holds the cover tab 22' to its adjoining closure tab 26 while allowing it to be removed upon intentional separation, as illustrated in FIG. 5. The release liner 34 is typically attached to the cover tab 22 or 22' and is comprised of a material, such as a silicone material, which is adapted to removably adhere the cover tab 22 or 22' to the adhesive portion of the closure tab 24 or 24'. The release liner 34 is sufficiently thin so as not to present problems as the elongated strip of bracelets are fed through the printer.

Typically, at least one of the layers of the sheet 30 will be capable of receiving imprinted information thereon. In the illustrated embodiment, sheet 30 would be comprised of a printable material, such as synthetic thermal label stock, which could be fed through a printer 14 and have information printed thereon for identification purposes and the like. In a particularly preferred embodiment, the bracelet or band 10 is composed of a direct thermal label stock laminated on a silicone coated polystyrene liner.

In order to manufacture the detachable bracelets in accordance with a particularly preferred embodiment of the present invention, a sheet 30 is coated with an adhesive 32 which is sufficient strong so as to create a semi-permanent or non-removable bond between the sheets 28 and 30 when assembled. At predetermined distances, the release liner 34 is applied either to the top of the adhesive layer 32, or the underside of the top sheet 28. The area or length of the applied silicone layer corresponds to the general size of the adhesive portion 24 of the closure tab 26. For example, for a bracelet 10 having an overall length of twelve inches, 0.5 inches at an end thereof, for example, will include the silicone release liner layer 34. Thus, along the adhesive layer 32 or the upper sheet 28, a one-half inch release liner layer 34 will be applied so as to create a pattern along the length of the strip. The sheets 28 and 30 are brought together so as to be bonded to one another, except at those localized areas where the silicone release liner layers 34 are preset.

Score lines 36 and 38 are formed in each sheet 28 and 30 where the identification bracelets 10 and 10' overlap in end-to-end fashion. The score lines 36 and 38 are sufficiently deep so as to render the identification bracelets 10 and 10' detachably connected to one another. Thus, score line 36 will extend through bottom sheet 30 as well as through the adhesive layer 32, and release liner layer 34, if necessary. However, score line 38 preferably only extends through upper sheet 28 (and release liner layer 34, if necessary), but not through adhesive layer 32 nor bottom sheet 30, as illustrated in FIGS. 4 and 5. Such score lines 36 and 38 may be comprised of a plurality of perforations, as is well known in the art. One score line 38 defines the end of the cover tab 22'. The other score line 36, formed in the opposite layer 30, is offset from the first score line 36, as illustrated in FIG. 4, and defines the end of the closure tab 26. Given the arrangement of the score lines 36 and 38 and the opposing layers 28 and 30, it will be appreciated that the cover tab 22' and the adhesive portion 24 of the closure tab 26 are substantially equal in size and complimentary in configuration. This arrangement also provides a single thickness of the detachably connected bracelets 10 and 10', permitting them to be easily fed through printer 14. Together, score lines 36 and 38 cooperatively form the abutting ends of the bracelets 10 and 10'.

When the bracelets 10 and 10' are separated from one another along the score lines 36 and 38, a flap of outer sheet 28, typically comprised of a plastic material such as polystyrene, extends from the end of identification bracelet 10 and defines the cover tab 22. Once bracelet 10 is separated from the adjoining bracelet 10', the adhesive portion 24 of the closure tab 26 of identification bracelet 10 is exposed.

Figure 6:
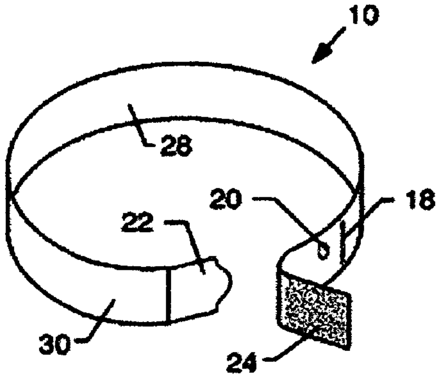
FIG. 6 is a perspective view of an identification bracelet used in accordance with the present invention being moved into a closed position.
Figure 7:
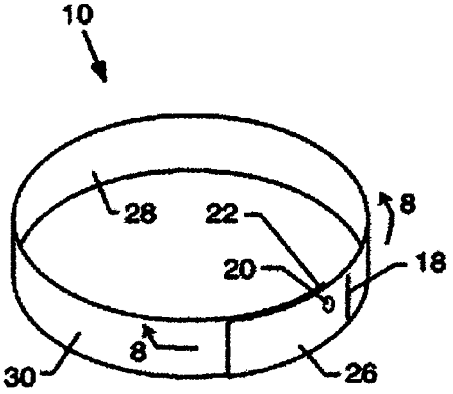
FIG. 7 is a perspective view similar to FIG. 6, illustrating the identification bracelet having a closure tab thereof adhered onto the bracelet to close the bracelet.
Figure 8:
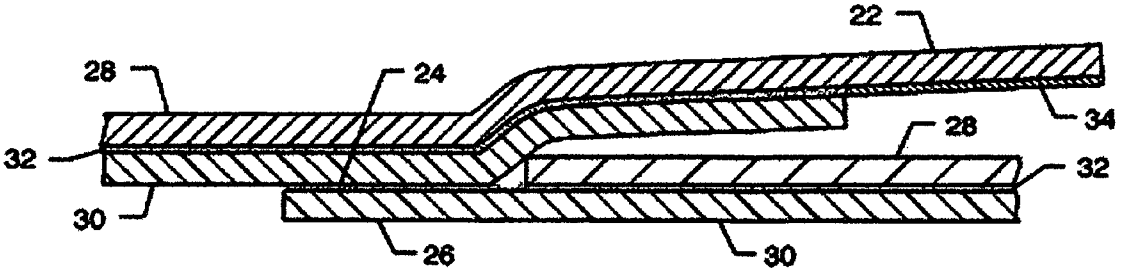
FIG. 8 is an enlarged cross-sectional view taken generally along 8-8 of FIG. 7.

As the adhesive portion 24 of the detached identification bracelet 10 is exposed, the identification bracelet 10 can be encircled about an object to be identified, such as a user's wrist, and the adhesive portion 24 of the closure tab 26 adhered onto a portion of the identification bracelet to close the identification bracelet about the object to be identified, as illustrated in FIGS. 6 and 7. Typically, the adhesive portion 24 will be adhered onto an outer surface 30 of the identification bracelet such that the cover tab 22, which remains with the end of the bracelet 10, is disposed within the closed identification bracelet, as illustrated in FIGS. 7 and 8.

The bracelet 10 thereby remains a unitary article, generating no separate refuse to be disposed of at the time the bracelet 10 is applied to the object. The bracelet 10 of the present invention also eliminates the need for somewhat complicated partial removal of a closure member or release liner from an adhesive area to enclose the band bottom object. The bracelet 10 of the present invention also eliminates the possibility of the separate sheets 28 and 30 becoming completely separated from one another when creating the band to encircle the object, as is the case with prior identification bracelets.

Although several embodiments have been described in detail for purposes of illustration, various modifications may be made without departing from the scope and spirit of the invention. Accordingly, the invention is not be limited, except as by the appended claims.

What is claimed is:

1. A plurality of identification bracelets detachably connected to one another comprising:

a first bracelet comprising first and second diametrically opposed outer sheets, the first sheet having a portion extending beyond a first end of the second sheet and defining a cover tab, and the second sheet extending beyond an end of the first sheet generally opposite the cover tab and defining a closure tab having an adhesive portion, the first and second outer sheets being non-removably bonded together substantially between the cover tab and closure tab; and a second bracelet comprising first and second diametrically opposed outer sheets, the first sheet having a portion extending beyond a first end of the second sheet and defining a cover tab removably overlying the adhesive portion of the closure tab of the first bracelet, and the second sheet extending beyond an end of the first sheet generally opposite the cover tab and defining a closure tab having an adhesive portion, the first and second outer sheets of the second bracelet being non-removably bonded together substantially between the cover tab and closure tab of the second bracelet;

whereby upon separating the first bracelet from the second bracelet, the adhesive portion of closure tab of the first bracelet is exposed and the cover tab of the second bracelet remains with the second bracelet and the exposed adhesive portion of the closure tab of the first bracelet is adhered onto a portion of the first bracelet as it is moved from an open position to a closed position encircling an object to be identified.

2. The bracelets of claim 1, including a release liner disposed between the cover tab of the second bracelet and the adhesive portion of the closure tab of the first bracelet and adapted to removably adhere the cover tab to the adhesive portion of the closure tab.

3. The bracelets of claim 2, wherein the release liner is attached to the cover tab.

4. The bracelets of claim 2, wherein the release liner comprises a silicone material.

5. The bracelets of claim 1, wherein the cover tab and the adhesive portion of the closure tab of each bracelet are substantially equal in area.

6. The bracelets of claim 1, wherein a score line formed in the first outer sheet defines the cover tab of the bracelet, and an offset score line formed in the second outer sheet defines the end of the bracelet.

7. The bracelets of claim 6, wherein the score lines comprise a plurality of perforations.

8. The bracelets of claim 1, wherein the bracelets comprise a plurality of bracelets detachably connected end-to-end to form an elongated strip.

9. The bracelets of claim 1, wherein the first and second outer sheets are each comprised of one or more layers of material.

10. The bracelets of claim 9, wherein at least one of the layers of the first or second outer sheet is comprised of a material adapted to be printed thereon.

11. The bracelets of claim 1, including an adhesive layer non-removably bonding the first and second outer sheets.

12. The bracelets of claim 11, wherein the adhesive layer extends beyond the first sheet towards the end of the second sheet to comprise the adhesive portion of the closure tab.

13. The bracelets of claim 11, wherein the adhesive layer extends beyond the first sheet towards the end of the second sheet to comprise the adhesive portion of the closure tab.

14. A plurality of identification bracelets detachably connected to one another comprising:

a first bracelet comprising first and second diametrically opposed outer sheets, the first sheet having a portion extending beyond a first end of the second sheet and defining a cover tab, and the second sheet extending beyond an end of the first sheet generally opposite the cover tab and defining a closure tab having an adhesive portion, the first and second outer sheets being non-removably bonded together substantially between the cover tab and closure tab; and a second bracelet comprising first and second diametrically opposed outer sheets, the first sheet having a portion extending beyond a first end of the second sheet and defining a cover tab removably overlying the adhesive portion of the closure tab of the first bracelet, and the second sheet extending beyond an end of the first sheet generally opposite the cover tab and defining a closure tab having an adhesive portion, the first and second outer sheets of the second bracelet being non-removably bonded together substantially between the cover tab and closure tab of the second bracelet;

a release liner disposed between the cover tab of the second bracelet and the adhesive portion of the closure tab of the first bracelet and adapted to removably adhere the cover tab to the adhesive portion of the closure tab;

wherein the cover tab and the adhesive portion of the closure tab of each bracelet are substantially equal in area;

whereby upon separating the first bracelet from the second bracelet, the adhesive portion of closure tab of the first bracelet is exposed and the cover tab of the second bracelet remains with the second bracelet and the exposed adhesive portion of the closure tab of the first bracelet is adhered onto a portion of the first bracelet as it is moved from an open position to a closed position encircling an object to be identified.

15. The bracelets of claim 14, wherein the release liner comprises a silicone material attached to the cover tab.

16. The bracelets of claim 14, wherein a score line formed in the first outer sheet defines the cover tab of the bracelet, and an offset score line formed in the second outer sheet defines the end of the bracelet.

17. The bracelets of claim 14, wherein the bracelets comprise a plurality of bracelets detachably connected end-to-end to form an elongated strip.

18. The bracelets of claim 14, including an adhesive layer non-removably bonding the first and second outer sheets.

19. A plurality of identification bracelets detachably connected to one another forming an elongated strip comprising:

a first bracelet comprising first and second diametrically opposed outer sheets, the first sheet having a portion extending beyond a first end of the second sheet and defining a cover tab, and the second sheet extending beyond an end of the first sheet generally opposite the cover tab and defining a closure tab having an adhesive portion;

a second bracelet comprising first and second diametrically opposed outer sheets, the first sheet having a portion extending beyond a first end of the second sheet and defining a cover tab removably overlying the adhesive portion of the closure tab of the first bracelet, and the second sheet extending beyond an end of the first sheet generally opposite the cover tab and defining a closure tab having an adhesive portion;

an adhesive layer non-removably bonding the first and second outer sheets, the adhesive layer extending beyond the first sheet towards the end of the second sheet to comprise the adhesive portion of the closure tab; and a release liner disposed between the cover tab of the second bracelet and the adhesive portion of the closure tab of the first bracelet and adapted to removably adhere the cover tab to the adhesive portion of the closure tab;

wherein the cover tab and the adhesive portion of the closure tab of each bracelet are substantially equal in area;

whereby upon separating the first bracelet from the second bracelet, the adhesive portion of closure tab of the first bracelet is exposed and the cover tab of the second bracelet remains with the second bracelet and the exposed adhesive portion of the closure tab of the first bracelet is adhered onto a portion of the first bracelet as it is moved from an open position to a closed position encircling an object to be identified.

20. The bracelets of claim 19, wherein a score line formed in the first outer sheet defines the cover tab of the bracelet, and an offset score line formed in the second outer sheet defines the end of the bracelet.

21. The bracelets of claim 19, wherein the release liner comprises a silicone material attached to the cover tab.

* * * * *